(12) United States Patent
Ooshima et al.

(10) Patent No.: US 10,640,532 B2
(45) Date of Patent: May 5, 2020

(54) CRYSTAL OF REDUCED GLUTATHIONE

(71) Applicants: University Public Corporation Osaka, Osaka-shi, Osaka (JP); Kyowa Hakko Bio Co., Ltd., Tokyo (JP)

(72) Inventors: Hiroshi Ooshima, Osaka (JP); Koichi Igarashi, Osaka (JP); Hiroshi Nagano, Tokyo (JP); Akihiro Fujimoto, Tokyo (JP); Kenta Fukumoto, Tokyo (JP); Kazunari Fukumoto, Tokyo (JP); Tomoya Yokoi, Tokyo (JP)

(73) Assignees: University Public Corporation Osaka, Osaka (JP); Kyowa Hakko Bio Co., Ltd., Tokyo (JP)

( * ) Notice: Subject to any disclaimer, the term of this patent is extended or adjusted under 35 U.S.C. 154(b) by 0 days.

(21) Appl. No.: 15/563,581

(22) PCT Filed: Mar. 31, 2016

(86) PCT No.: PCT/JP2016/060831
§ 371 (c)(1),
(2) Date: Sep. 30, 2017

(87) PCT Pub. No.: WO2016/159317
PCT Pub. Date: Oct. 6, 2016

(65) Prior Publication Data
US 2018/0094025 A1  Apr. 5, 2018

(30) Foreign Application Priority Data
Mar. 31, 2015 (JP) .................................. 2015-074084

(51) Int. Cl.
*C07K 5/02* (2006.01)
*B01D 9/00* (2006.01)
*B01D 9/04* (2006.01)

(52) U.S. Cl.
CPC ............ *C07K 5/0215* (2013.01); *B01D 9/005* (2013.01); *B01D 9/0036* (2013.01); *B01D 9/0054* (2013.01); *B01D 9/0004* (2013.01); *B01D 9/04* (2013.01); *B01D 2009/009* (2013.01)

(58) Field of Classification Search
None
See application file for complete search history.

(56) References Cited

U.S. PATENT DOCUMENTS

| 2004/0250751 A1 | 12/2004 | Shimose et al. |
| 2010/0035905 A1 | 2/2010 | Schmidt et al. |
| 2010/0099847 A1 | 4/2010 | Shimose et al. |
| 2013/0035470 A1 | 2/2013 | Kimura et al. |
| 2013/0053296 A1 | 2/2013 | Baranyai |
| 2016/0002797 A1 | 1/2016 | Fukumoto et al. |

FOREIGN PATENT DOCUMENTS

| CN | 101074202 A | 11/2007 |
| JP | S57-035548 A | 2/1982 |
| JP | S57-035549 A | 2/1982 |
| JP | S61-027999 A | 2/1986 |
| JP | H03-220392 A | 9/1991 |
| JP | 2005-015682 A | 1/2005 |
| JP | 2010-505918 A | 2/2010 |
| JP | 2013-516502 A | 5/2013 |
| WO | WO 2003/035674 A1 | 5/2003 |
| WO | WO 2008/047792 A1 | 4/2008 |
| WO | WO 2011/132724 A1 | 10/2011 |
| WO | WO 2014/133129 A1 | 9/2014 |

OTHER PUBLICATIONS

Translation of Haruhiko et al, JP 61-27999 (1986).*
List of pKas of amino acids from Keene university, http://academics.keene.edu/rblatchly/Chem220/hand/npaa/aawpka.htm, downloaded Jan. 14, 2018.*
Rebbeor et al., "ATP-dependent transport of reduced glutathione in yeast secretory vesicles," *Biochem. J.*, 334(3): 723-729 (1998).
Japanese Patent Office, International Search Report in International Patent Application No. PCT/JP2016/060831 (dated Jul. 5, 2016).
Caira, "Crystalline Polymorphism of Organic Compounds," *Topics in Current Chemistry*, 198: 163-208 (1998).
European Patent Office, Extended European Search Report in European Patent Application No. 16773197.5 (dated Oct. 16, 2018).
Japanese Patent Office, International Preliminary Report on Patentability in International Patent Application No. PCT/JP2016/060831 (dated Oct. 3, 2017).

* cited by examiner

*Primary Examiner* — Fred H Reynolds
(74) *Attorney, Agent, or Firm* — Leydig, Voit & Mayer, Ltd.

(57) ABSTRACT

The present invention provides a crystal of reduced glutathione that is stable, and is easy to process, and a method for producing the crystal. According to the present invention, a crystal of a metal salt of reduced glutathione is produced by suspending an amorphous solid of a metal salt of reduced glutathione in a hydrophobic organic solvent, and adding water to the resulting suspension to precipitate a crystal of a metal salt of reduced glutathione.

9 Claims, 2 Drawing Sheets

CRYSTAL OF REDUCED GLUTATHIONE

CROSS-REFERENCE TO RELATED APPLICATIONS

This patent application is the U.S. national phase of International Patent Application No. PCT/JP2016/060831, filed Mar. 31, 2016, which claims the benefit of Japanese Patent Application No. 2015-074084, filed on Mar. 31, 2015, which are incorporated by reference in their entireties herein.

TECHNICAL FIELD

The present invention relates to a crystal of reduced glutathione useful for, for example, products such as health-aid food, pharmaceuticals, and cosmetics, or as a raw material, an intermediate, or the like of such products.

BACKGROUND ART

Reduced glutathione (γ-L-glutamyl-L-cysteinyl-glycine) is a substance occurring in a wide range of living organisms, and is known to have a detoxification effect in the liver, in addition to acting as a coenzyme. This has made reduced glutathione useful in a wide range of applications including products such as pharmaceuticals, health-aid food, and cosmetics, and raw materials, intermediates, or the like of such products.

For ease of handling, a powder is the desired form of reduced glutathione used for such products, raw materials, and intermediates. However, the noncrystalline (amorphous) form of reduced glutathione obtained through a common dry powder manufacturing method such as freeze drying and spray drying has high hygroscopicity and insufficient fluidity, and is not suited for processing.

A crystal of a free form of reduced glutathione is known (Patent Document 1). However, free-form crystals have low solubility, and are not suited for liquid preparations. The acidic nature of free-form crystals also requires care for processing. This has created a demand for a crystal of reduced glutathione that has good preservation stability, and is easy to process.

A monohydrate (Patent Document 2) and a hexahydrate (Patent Document 3) of a free oxidized glutathione (a dimer of glutathione) with a disulfide linkage between reduced glutathione molecules are known. However, a hydrate crystal, and a salt crystal of reduced glutathione are not known.

RELATED ART

Patent Document

Patent Document 1: WO2008/047792
Patent Document 2: WO2003/035674
Patent Document 3: WO2011/132724

DISCLOSURE OF INVENTION

Problems to be Solved by the Invention

It is an object of the present invention to provide a metal salt crystal of reduced glutathione useful for, for example, products such as health-aid food, pharmaceuticals, and cosmetics, or as a raw material, an intermediate, or the like of such products.

Means for Solving the Problems

The present invention relates to the following (1) to (22).
(1) A crystal of a metal salt of reduced glutathione.
(2) The crystal of a metal salt of reduced glutathione described in (1) above, which is a crystal of a salt of reduced glutathione and a metal selected from the group consisting of sodium, potassium, calcium, and magnesium.
(3) The crystal of a metal salt of reduced glutathione described in (1) above, which is a crystal of a salt of reduced glutathione and sodium (hereinafter, referred to as "reduced glutathione-sodium salt") (hereinafter, referred to as "reduced glutathione-sodium salt crystal").
(4) The crystal described in (3) above, wherein the reduced glutathione-sodium salt crystal is a monohydrate crystal of a reduced glutathione-sodium salt.
(5) The crystal described in (4) above, which has peaks at a diffraction angle (2θ) of 19.90°±0.20°, 25.58°±0.20°, and 26.88°±0.20° in powder X-ray diffraction.
(6) The crystal described in (5) above, which has peaks also at a diffraction angle (2θ) of 20.16°±0.20°, 24.68°±0.20°, 26.30°±0.20°, 27.68°±0.20°, and 33.20±0.20° in powder X-ray diffraction.
(7) The crystal described in (6) above, which has peaks also at a diffraction angle (2θ) of 17.90°±0.20°, 20.86°±0.20°, 22.10°±0.20°, and 25.30°±0.20° in powder X-ray diffraction.
(8) The crystal described in (7) above, which has peaks also at a diffraction angle (2θ) of 6.42±0.20°, 18.90±0.20°, and 29.30±0.20° in powder X-ray diffraction.
(9) The crystal described in any one of (4) to (8) above, which has the following brief unit cell parameters: a=27.881 Å, b=10.818 Å, c=4.881 Å, α=90°, β=90°, γ=90°, V=1472.2 Å$^3$, and Z=4 with a space group P2$_1$2$_1$2$_1$ (#19), as measured by single-crystal X-ray structure analysis at −173° C.
(10) The crystal described in (3) above, wherein the reduced glutathione-sodium salt crystal is an anhydrous crystal of a reduced glutathione-sodium salt.
(11) The crystal described in (10) above, which has peaks at a diffraction angle (2θ) of 25.92°±0.20°, 20.28°±0.20°, and 27.28°±0.20° in powder X-ray diffraction.
(12) The crystal described in (11) above, which has peaks also at a diffraction angle (2θ) of 20.52°±0.20°, 25.02°±0.20°, 21.26°±0.20°, 26.66°±0.20°, and 28.08±0.20° in powder X-ray diffraction.
(13) The crystal described in (12) above, which has peaks also at a diffraction angle (2θ) of 22.48°±0.20°, 33.56°±0.20°, 19.70°±0.20°, and 18.32°±0.20° in powder X-ray diffraction.
(14) The crystal described in (13) above, which has peaks also at a diffraction angle (2θ) of 19.26±0.20°, 28.74±0.20°, and 29.64±0.20° in powder X-ray diffraction.
(15) A method for producing a crystal of a metal salt of reduced glutathione,
the method comprising suspending an amorphous solid of a metal salt of reduced glutathione in a hydrophobic organic solvent, and adding water to the resulting suspension to precipitate a crystal of a metal salt of reduced glutathione.
(16) The method for producing a crystal of a metal salt of reduced glutathione described in (15) above, wherein the hydrophobic organic solvent is hexane or toluene.
(17) A method for producing a crystal of a metal salt of reduced glutathione,
the method comprising suspending an amorphous solid of a metal salt of reduced glutathione in a hydrophobic organic solvent, and adding an aqueous solution of methanol or ethanol to the resulting suspension to precipitate a crystal of a metal salt of reduced glutathione.

(18) A method for producing a crystal of a metal salt of reduced glutathione, the method comprising dissolving a free form of reduced glutathione in a metal hydroxide aqueous solution, and adjusting the pH of the solution to 5.0 to 8.0 to obtain an aqueous solution of a metal salt of reduced glutathione; concentrating the resulting aqueous solution, and gradually adding a C1 to C6 alcohol to the concentrated aqueous solution in small portions in an amount 0.1 to 3 times the amount of the concentrated aqueous solution; and adding a crystal of a metal salt of reduced glutathione as a seed crystal to precipitate a crystal of a metal salt of reduced glutathione.

(19) The method for producing a crystal of a metal salt of reduced glutathione described in (15), (17), or (18) above, wherein the crystal of a metal salt of reduced glutathione is a monohydrate crystal of a salt of reduced glutathione and a metal selected from the group consisting of sodium, potassium, calcium, and magnesium.

(20) The method for producing a crystal of a metal salt of reduced glutathione described in (15), (17), or (18) above, wherein the crystal of a metal salt of reduced glutathione is a monohydrate crystal of a reduced glutathione-sodium salt.

(21) The method for producing a crystal of a metal salt of reduced glutathione described in (18) above, wherein the C1 to C6 alcohol is methanol or ethanol.

(22) A method for producing an anhydrous crystal of a reduced glutathione-sodium salt, the method comprising drying a monohydrate crystal of a reduced glutathione-sodium salt at 80° C. or more for at least 3 hours.

Effects of the Invention

According to the present invention, a metal salt crystal of reduced glutathione useful for, for example, products such as health-aid food, pharmaceuticals, and cosmetics, or as a raw material, an intermediate, or the like of such products is provided.

EMBODIMENTS FOR CARRYING OUT THE INVENTION

1. Crystal of Metal Salt of Reduced Glutathione of the Present Invention

The crystal of a metal salt of reduced glutathione of the present invention may be an anhydrous crystal or a hydrate crystal. Preferred is a hydrate crystal, more preferably a monohydrate crystal. Monohydrate crystals are preferred for their desirable preservation stability.

The crystal of a metal salt of reduced glutathione of the present invention may be a crystal having crystal polymorphism, such as α crystals and β crystals. Preferred are a crystals. The crystal may be one in which the proportion of α crystal in the total metal salt crystal of reduced glutathione is preferably 95% or more, more preferably 97% or more, further preferably 98% or more, even more preferably 99% or more, particularly preferably 99.5% or more, most preferably 99.9% or more.

The metal in the crystal of a metal salt of reduced glutathione of the present invention is not limited, as long as the crystal is a crystal of a salt of reduced glutathione and a metal. Preferably, the metal is any of metals that belong to alkali metals or alkali earth metals, preferably a metal selected from the group consisting of sodium, potassium, calcium, and magnesium, further preferably sodium.

The crystal of a metal salt of reduced glutathione of the present invention may be a crystal with numbers of molecules that make the metal ions equivalent to glutathione. Specifically, for example, the metal ion valency is typically 0.5 to 2, preferably 0.8 to 1.2, more preferably 1.0 with respect to the glutathione ion valency.

The crystal of a metal salt of reduced glutathione of the present invention may be, for example, a crystal with a pH of typically 5.0 to 8.0, more preferably 5.5 to 7.5, further preferably 6.0 to 7.0.

When the crystal of a salt of reduced glutathione and sodium of the present invention (hereinafter, such a salt will be referred to as "reduced glutathione-sodium salt", and such a crystal will be referred to as "reduced glutathione-sodium salt crystal") is a monohydrate crystal, the crystal has peaks at a diffraction angle (2θ) of 19.90°±0.20°, 25.58°±0.20°, and 26.88°±0.20° in powder X-ray diffraction using CuKα as an X-ray source.

Preferably, the crystal has peaks at a 2θ of 20.16°±0.20°, 24.68°±0.20°, 26.30°±0.20°, 27.68°±0.20°, and 33.20±0.20°.

More preferably, the crystal also has peaks at a (2θ) of 17.90°±0.20°, 20.86°±0.20°, 22.10°±0.20°, and 25.30°±0.20°.

Further preferably, the crystal also has peaks at a 2θ of 6.42±0.20°, 18.90±0.20°, and 29.30±0.20°.

Figure 1:
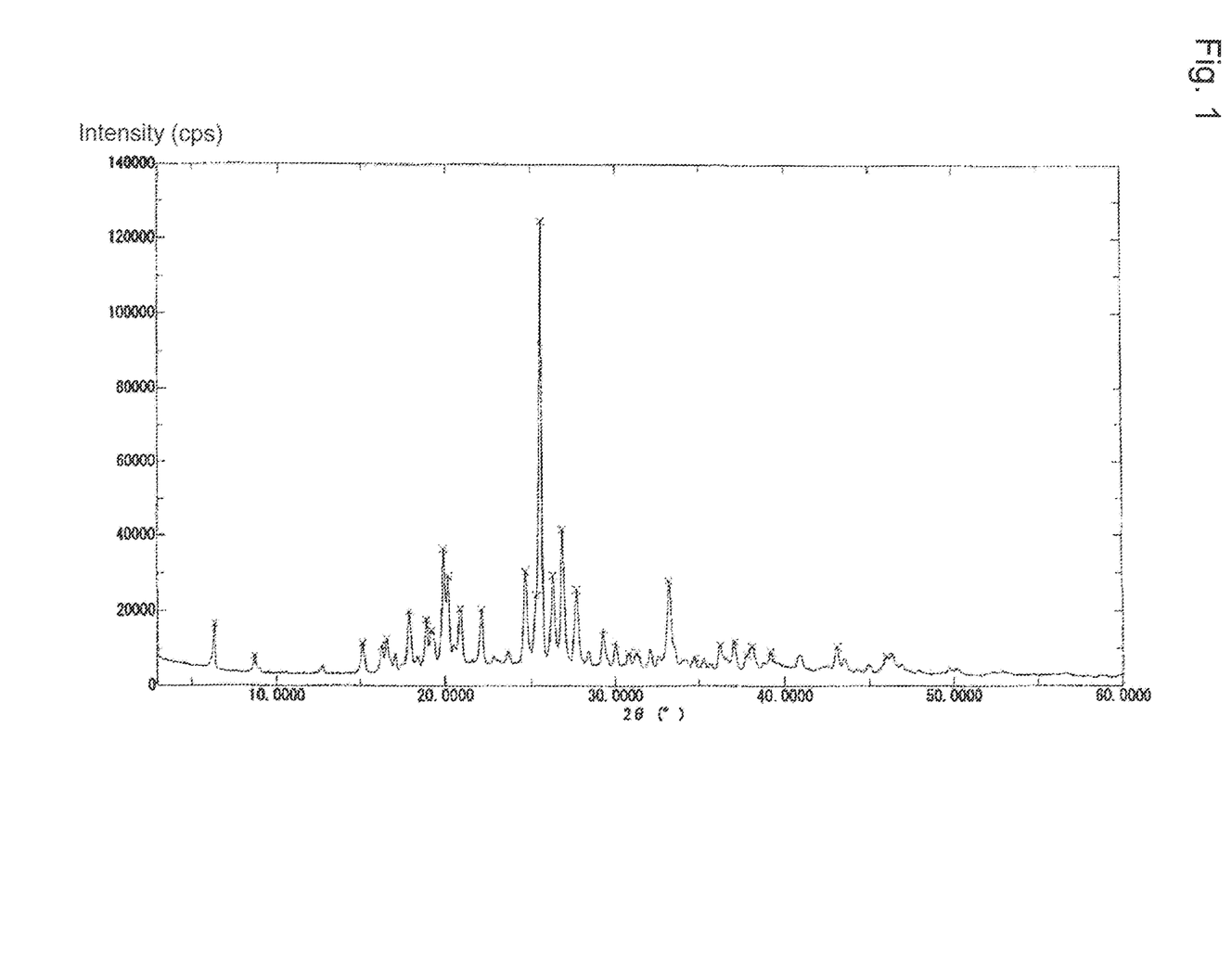
FIG. 1 is a diagram showing a powder X-ray diffraction peak pattern of a monohydrate crystal of a reduced glutathione-sodium salt, in which the vertical axis represents intensity (unit: cps), and the horizontal axis represents diffraction angle (2θ; (unit: °).

Most preferably, the crystal is a crystal specified by the numbers shown in Table 1, and that has the diffraction pattern shown in FIG. 1.

TABLE 1

| 2θ (°) | Intensity (cps) | Relative intensity |
| --- | --- | --- |
| 6.42 | 16472 | 14 |
| 8.76 | 7998 | 7 |
| 15.14 | 11593 | 10 |
| 16.30 | 10815 | 9 |
| 16.62 | 12486 | 11 |
| 17.90 | 19992 | 17 |
| 18.90 | 17687 | 15 |
| 19.22 | 14723 | 12 |
| 19.90 | 36253 | 30 |
| 20.16 | 29279 | 24 |
| 20.86 | 20508 | 17 |
| 22.10 | 20396 | 17 |
| 23.66 | 9100 | 8 |
| 24.68 | 30485 | 25 |
| 25.30 | 24063 | 20 |
| 25.58 | 124573 | 100 |
| 26.30 | 29380 | 24 |
| 26.88 | 41585 | 34 |
| 27.68 | 25615 | 21 |
| 29.30 | 14927 | 12 |
| 30.00 | 11685 | 10 |
| 30.80 | 8764 | 8 |
| 31.30 | 8802 | 8 |
| 33.20 | 27992 | 23 |

TABLE 1-continued

| 2θ (°) | Intensity (cps) | Relative intensity |
|---|---|---|
| 34.74 | 7462 | 6 |
| 36.22 | 11080 | 9 |
| 37.09 | 11946 | 10 |
| 37.80 | 8216 | 7 |
| 38.10 | 10661 | 9 |
| 39.18 | 9098 | 8 |
| 43.04 | 10585 | 9 |
| 46.00 | 7883 | 7 |
| 46.34 | 8484 | 7 |

The following analyzer, and measurement conditions may be used for powder X-ray diffraction, for example. By using the horizontal-sample multi-purpose X-ray diffraction device Ultima IV available from Rigaku, a sample is irradiated with non-monochromatic X-rays from a copper target sealed tube used as an X-ray source, and diffracted X-rays derived from CuKα rays (wavelength 1.541 Å) are detected using an energy resolving detector.

Preferably, the monohydrate crystal of a reduced glutathione-sodium salt of the present invention is more specifically A crystal having the following brief unit cell parameters: a=27.881 Å, b=10.818 Å, c=4.881 Å, α=90°, β=90°, γ=90°, V=1472.2 Å$^3$, and Z=4 with a space group $P2_12_12_1$ (#19), as measured by single-crystal X-ray structure analysis at −173° C.

More preferably, the monohydrate crystal of a reduced glutathione-sodium salt of the present invention is a crystal specified by the numbers shown in Table 2 as measured by single-crystal X-ray structure analysis at −173° C.

TABLE 2

| Crystal data | |
|---|---|
| Chemical formula | Na$^+$•(C$_{10}$H$_{15}$N$_3$O$_8$S)$^-$•H$_2$O |
| M$_r$ | 347.32 |
| Crystal system, space group | Orthorhombic, $P2_12_12_1$ |
| Temperature (K) | 100 |
| a, b, c (Å) | 27.881 (14), 10.818 (5), 4.881 (2) |
| V (Å$^3$) | 1472.2 (12) |
| Z | 4 |
| Emission type | CuKα |
| μ (mm$^{-1}$) | 2.63 |
| Crystal size (mm) | 0.16 × 0.04 × 0.03 |
| Data Collection | |
| Diffractometer | Agilent SuperNova CCD diffractometer |
| Absorption correction | None |
| Number of observed independent [I > 2σ (I)] reflections | 5142, 2834, 1237 |
| R$_{int}$ | 0.1442 |
| (sinθ/λ)$_{max}$(Å$^{-1}$) | 0.625 |
| Refinement | |
| R[F$^2$ > 2σ(F$^2$)], wR(F$^2$), S | 0.1106, 0.3262, 1.006 |
| Number of reflections | 2834 |
| Number of parameters | 217 |
| H atom process | H-atom parameters constrained |
| Δρ$_{max}$*, Δρ$_{min}$ (e Å$^{-3}$) | 0.46, −0.47 |
| Absolute structure | Flack x determined using 1119 Friedel pairs (Flack, 1983) |
| Absolute structure parameter | −0.12 (11) |

A structure analysis by a single-crystal X-ray diffraction device (SXRD) may be used to determine the crystal structure of the metal salt of reduced glutathione of the present invention. A single crystal of a metal salt of reduced glutathione is set on a diffractometer, and the diffraction image is measured in a room temperature atmosphere or under a stream of an inert gas of a predetermined temperature, using X-rays of a predetermined wavelength. A monocrystalline structure can then be obtained from a combination of the plane index and the diffraction intensity calculated from the diffraction image, after structure determination by direct method, and structure refinement by least squares method [Acta Cryst. A64, 112 (2008)]. The single-crystal X-ray structure analyzer SuperNova available from Agilent Technologies may be used as the single-crystal X-ray diffraction device, for example.

Specifically, when the crystal of a metal salt of reduced glutathione of the present invention is an anhydrous crystal, the crystal has peaks at a diffraction angle (2θ) of 25.92°±0.20°, 20.28°±0.20°, and 27.28°±0.20° in powder X-ray diffraction using CuKα as an X-ray source.

Preferably, the crystal also has peaks at a diffraction angle (2θ) of 20.52°±0.20°, 25.02°±0.20°, 21.26°±0.20°, 26.66°±0.20°, and 28.08±0.20°.

More preferably, the crystal also has peaks at a diffraction angle (2θ) of 22.48°±0.20°, 33.56°±0.20°, 19.70°±0.20°, and 18.32°±0.20°.

Further preferably, the crystal also has peaks at a diffraction angle (2θ) of 19.26±0.20°, 28.74±0.20°, and 29.64±0.20°.

Figure 2:
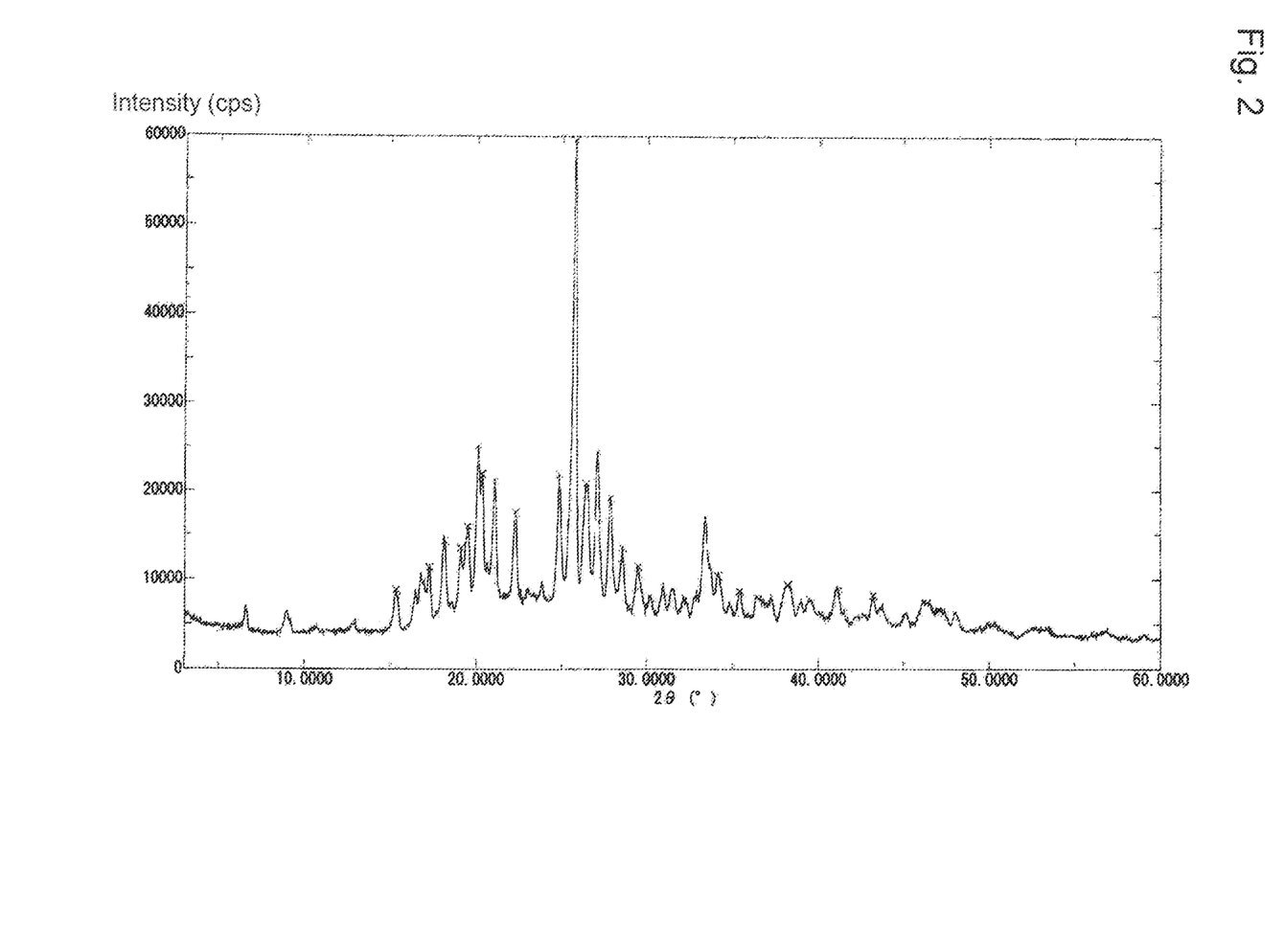
FIG. 2 is a diagram showing a powder X-ray diffraction peak pattern of an anhydrous crystal of a reduced glutathione-sodium salt, in which the vertical axis represents intensity (unit: cps), and the horizontal axis represents diffraction angle (2θ; (unit: °).

Most preferably, the crystal is an anhydrous crystal of a reduced glutathione-sodium salt specified by the numbers shown in Table 3, and that has the diffraction pattern shown in FIG. 2.

TABLE 3

| 2θ (°) | Intensity (cps) | Relative intensity |
|---|---|---|
| 15.54 | 5983 | 13 |
| 17.46 | 8167 | 18 |
| 18.32 | 10533 | 23 |
| 19.26 | 10458 | 23 |
| 19.70 | 11833 | 26 |
| 20.28 | 19883 | 44 |
| 20.52 | 17642 | 39 |
| 21.26 | 15867 | 35 |
| 22.48 | 13567 | 30 |
| 25.02 | 16358 | 36 |
| 25.92 | 46167 | 100 |
| 26.66 | 16067 | 35 |
| 27.28 | 20175 | 44 |
| 28.08 | 14058 | 31 |
| 28.74 | 9308 | 21 |
| 29.64 | 8608 | 19 |
| 33.56 | 13100 | 29 |
| 34.38 | 8008 | 18 |
| 35.58 | 6108 | 14 |
| 38.40 | 7167 | 16 |
| 41.18 | 6608 | 15 |
| 43.40 | 5750 | 13 |

2. Method of Production of Crystal of Metal Salt of Reduced Glutathione of Present Invention Method of Production of Monohydrate Crystal of Metal Salt of Reduced Glutathione (1) Production Method by Crystal Transformation The production method of the present invention may be a method for producing a monohydrate crystal of a metal salt of reduced glutathione comprising the step of suspending an amorphous solid of a salt of reduced glutathione and a metal in a hydrophobic organic solvent, and adding water to the resulting suspension to precipitate a monohydrate crystal of a metal salt of reduced glutathione.

The production method of the present invention may be a method for producing a monohydrate crystal of a metal salt of reduced glutathione comprising the step of suspending an amorphous solid of a salt of reduced glutathione and a metal in a hydrophobic organic solvent, and adding an aqueous solution of methanol or ethanol to the resulting suspension to precipitate a monohydrate crystal of a metal salt of reduced glutathione.

The amorphous solid of a salt of reduced glutathione and a metal may be obtained as follows. A metal hydroxide and water are added to a free form of reduced glutathione in equimolar amounts. After neutralization, the mixture is dried by being rapidly frozen using liquid nitrogen.

The free form of reduced glutathione may be amorphous or crystalline. The crystal may be purchased from Kyowa Hakko Bio Co., Ltd. The amorphous solid may be obtained by purifying reduced glutathione using a known method after preparing the reduced glutathione using the fermentation method (WO2008/126784) or the enzyme method [for example, Appl. Microbiol. Biotechnol., 66, 233 (2004), and JP-A-60-105499], followed by drying, for example, freeze drying or spray drying.

The metal hydroxide is preferably a hydroxide of an alkali metal or an alkali earth metal, particularly a hydroxide of a metal selected from the group consisting of sodium, potassium, calcium, and magnesium. The metal hydroxide is most preferably sodium hydroxide.

As an example, a metal hydroxide and water are added to reduced glutathione, and the mixture is stirred for typically 1 to 12 days, preferably 5 to 10 days, more preferably 7 days to completely dissolve the glutathione. After rapid cooling with liquid nitrogen, the product is dried with a commercially available freeze drier to obtain an amorphous solid of a salt of reduced glutathione and the metal.

The amorphous solid of a metal salt of reduced glutathione may be dispersed and suspended in a hydrophobic organic solvent, and water may be added to the resulting suspension to transform the metal salt of reduced glutathione from an amorphous state to a crystal.

The hydrophobic organic solvent may be, for example, hexane or toluene. The amorphous solid of a metal salt of reduced glutathione is dispersed in an amount of typically 5 to 100 mg, preferably 10 to 80 mg, more preferably 20 to 50 mg per milliliter of the hydrophobic organic solvent.

When in excess, the water added to the metal salt solution of reduced glutathione becomes a source of liquid droplets for the amorphous solid, and liquefies the amorphous solid. To prevent this, water is added in an amount of, for example, typically 1 to 20 preferably 2 to 15 more preferably 2 to 12 μL, particularly preferably 5 to 10 μl per milliliter of the hydrophobic organic solvent.

After addition of water, a monohydrate crystal of a metal salt of reduced glutathione can be obtained upon stirring the mixture. The monohydrate crystal of a metal salt of reduced glutathione is preferably a monohydrate crystal of a salt of reduced glutathione and a metal selected from the group consisting of sodium, potassium, calcium, and magnesium, more preferably a monohydrate crystal of a reduced glutathione-sodium salt. The crystal may be dried by, for example, drying under reduced pressure.

The monohydrate crystal of a metal salt of reduced glutathione also can be obtained by adding an aqueous solution of methanol or ethanol, instead of water.

The aqueous solution of methanol or ethanol may be added in an amount of, for example, 10 to 60 μL in terms of an amount of an 80% methanol or ethanol aqueous solution per milliliter of hydrophobic organic solvent. Considering the compatibility of methanol and ethanol with a hydrophobic organic solvent such as hexane, and the amount of water added to the hydrophobic organic solvent, a monohydrate crystal of a metal salt of reduced glutathione can be obtained with the concentration and the amount of an alcohol solution corresponding to 10 to 60 μl of an 80% methanol or ethanol aqueous solution.

(2) Crystal Production Method Using Seed Crystal

The monohydrate crystal of a metal salt of reduced glutathione obtained in (1) above can be used as a seed crystal to enable industrial production of a monohydrate crystal of a metal salt of reduced glutathione.

A free form of reduced glutathione is dissolved in a metal hydroxide aqueous solution. A metal salt aqueous solution of reduced glutathione is obtained by adjusting the pH to 5.0 to 8.0, and the aqueous solution is concentrated after filtration using, for example, a filter.

A C1 to C6 alcohol is gradually added after cooling the concentrated aqueous solution. After stirring the mixture, the monohydrate crystal of a metal salt of reduced glutathione is added as a seed crystal.

The precipitated crystals are aged, and, after cooling, the monohydrate crystal of a metal salt of reduced glutathione is separated. The separated crystal can then be dried to obtain a monohydrate crystal of a metal salt of reduced glutathione.

The monohydrate crystal of a metal salt of reduced glutathione is preferably a monohydrate crystal of a salt of reduced glutathione and a metal selected from the group consisting of sodium, potassium, calcium, and magnesium, more preferably a monohydrate crystal of a reduced glutathione-sodium salt.

The metal hydroxide is preferably a hydroxide of an alkali metal or an alkali earth metal, particularly a hydroxide of a metal selected from the group consisting of sodium, potassium, calcium, and magnesium. Most preferably, the metal hydroxide is sodium hydroxide.

The aqueous solution of a metal salt of reduced glutathione is obtained by dissolving a free form of reduced glutathione in the metal hydroxide aqueous solution, and adjusting the pH to typically 5.0 to 8.0, preferably 5.5 to 7.5, more preferably 6.0 to 7.0. The aqueous solution of a metal salt of reduced glutathione is concentrated under reduced pressure to a concentration of typically 400 to 900 g/L, preferably 500 to 850 g/L, more preferably 600 to 800 g/L.

The concentrated aqueous solution is cooled to typically 10 to 30° C., preferably 15 to 28° C., more preferably 20 to 25° C., and a C1 to C6 alcohol is gradually added in small portions. Preferably, methanol or ethanol is added in 0.1 to 3 times, preferably 0.5 to 2 times the amount of the concentrated aqueous solution, more preferably in about the same amount as the concentrated aqueous solution. Methanol or ethanol may be added at a rate of, for example, 1.0 to 2.0 ml/min when the concentrated aqueous solution is 100 ml.

The amount of the monohydrate crystal of a metal salt of reduced glutathione added as a seed crystal may be, for example, 0.1 to 5%, preferably 0.2 to 3%, more preferably 0.3 to 2% of the amount of reduced glutathione contained in the concentrated aqueous solution (an amount in terms of a free form).

The precipitated crystals can be aged by allowing the solution to stand at a temperature between room temperature and 80° C. after adding the seed crystal. Heat is applied at a rate of, for example, 20° C./h.

The aging time is not limited, and is, for example, preferably 30 minutes to 20 hours, more preferably 1 hour to 15 hours.

In the case of aging by heating, it is preferable to cool the solution, and age the crystals at the cooling temperature.

Cooling may be performed at a rate of, for example, 5° C./h. The aging temperature may be 15° C. to room temperature, more preferably 20 to 25° C.

The aging time is not limited, and is, for example, preferably 30 minutes to 5 hours, more preferably 1 hour to 3 hours.

After being aged, the crystals may be separated by filtration or centrifugation, and dried, for example, under reduced pressure to obtain the monohydrate crystal of a metal salt of reduced glutathione.

Method of Production of Anhydrous Crystal of Metal Salt of Reduced Glutathione

A white anhydrous crystal of a metal salt of reduced glutathione can be obtained by drying the monohydrate crystal of a metal salt of reduced glutathione obtained in the manner described above, using a known method, for example, such as drying under reduced pressure, vacuum drying, fluidized bed drying, and draught drying. In a preferred method, the monohydrate crystal of a metal salt of reduced glutathione is dried at 80° C. or more for at least 3 hours. Specifically, for example, an anhydrous crystal of a reduced glutathione-sodium salt can be obtained by draught drying the monohydrate crystal of a reduced glutathione-sodium salt at 105° C. for 20 hours.

EXAMPLES

Examples of the present invention are described below. The present invention, however, is not limited by the following Examples.

Example 1

Production 1 of Crystal of Metal Salt of Reduced Glutathione by Crystal Transformation
(1) Production of Amorphous Solid of Metal Salt of Reduced Glutathione Ultrapure water (50 mL), and 2 mol/L of sodium hydroxide aqueous solution (813 μL) were added to 0.5 g of a crystal of free reduced glutathione (Kyowa Hakko Bio Co., Ltd.), and the reduced glutathione was completely dissolved. A container containing the solution was placed in liquid nitrogen, and the solution was rapidly frozen. This was followed by drying under reduced pressure for at least 3 days in a freeze drier to obtain an amorphous solid of a reduced glutathione-sodium salt.
(2) Transformation to Metal Salt Crystal of Reduced Glutathione The amorphous solid of a reduced glutathione-sodium salt (50 mg) obtained in (1) above was dispersed in 1.0 mL of hexane, and the mixture was stirred for 7 days after adding 5 μL of water. The precipitated crystals were separated with a Nutsche filter, and dried under reduced pressure to obtain crystals of a reduced glutathione-sodium salt.

Example 2

Production 2 of Crystal of Metal Salt of Reduced Glutathione by Crystal Transformation An amorphous solid of a sodium salt of reduced glutathione (250 mg) obtained in the same manner as in (1) of Example 1 was dispersed in 5 mL of hexane, and the mixture was stirred for 7 days after adding 55 μL of an 80% ethanol aqueous solution. The precipitated crystals were separated with a Nutsche filter, and dried under reduced pressure to obtain crystals of a reduced glutathione-sodium salt.

Test Example 1

Powder X-Ray Diffraction Analysis

The reduced glutathione-sodium salt crystals obtained in Examples 1 and 2 were subjected to powder X-ray diffraction analysis.

The analysis was conducted under the following conditions, and the following measurement conditions were used for the crystal obtained in Example 1.

Analyzer: Horizontal-sample multi-purpose X-ray diffraction device Ultima IV available from Rigaku Measurement Conditions:

X-ray source: CuKα

Measurement wavelength: 1.541 Å

Kα rays were used without being monochromatized with a monochrometer

TABLE 4

| 2θ (°) | Intensity (cps) | Relative intensity |
| --- | --- | --- |
| 6.42 | 16472 | 14 |
| 8.76 | 7998 | 7 |
| 15.14 | 11593 | 10 |
| 16.30 | 10815 | 9 |
| 16.62 | 12486 | 11 |
| 17.90 | 19992 | 17 |
| 18.90 | 17687 | 15 |
| 19.22 | 14723 | 12 |
| 19.90 | 36253 | 30 |
| 20.16 | 29279 | 24 |
| 20.86 | 20508 | 17 |
| 22.10 | 20396 | 17 |
| 23.66 | 9100 | 8 |
| 24.68 | 30485 | 25 |
| 25.30 | 24063 | 20 |
| 25.58 | 124573 | 100 |
| 26.30 | 29380 | 24 |
| 26.88 | 41585 | 34 |
| 27.68 | 25615 | 21 |
| 29.30 | 14927 | 12 |
| 30.00 | 11685 | 10 |
| 30.80 | 8764 | 8 |
| 31.30 | 8802 | 8 |
| 33.20 | 27992 | 23 |
| 34.74 | 7462 | 6 |
| 36.22 | 11080 | 9 |
| 37.09 | 11946 | 10 |
| 37.80 | 8216 | 7 |
| 38.10 | 10661 | 9 |
| 39.18 | 9098 | 8 |
| 43.04 | 10585 | 9 |
| 46.00 | 7883 | 7 |
| 46.34 | 8484 | 7 |

FIG. 1 shows a chart diagram of the powder X-ray diffraction analysis.

The crystal obtained in Example 2 was also analyzed in the manner described above, and the chart diagram for the crystal obtained in Example 2 was compared with the chart diagram of FIG. 1. The results were very similar, confirming that the crystal obtained in Example 2 had the same crystal form as the crystal obtained in Example 1.

Test Example 2

Measurement of Moisture Content

The crystal obtained in Example 1 was analyzed by a thermal analysis under the following conditions.

Measurement device: Thermal analyzer TG/DTA, Model 6200 available from SSI Nanotechnologies (currently, Hitachi High-Technologies)

Measurement conditions: Moisture content was calculated from amounts of weight change under increasing temperatures of from 50° C. to 170° C. at a rate of temperature increase of 2° C./h An about 5% weight reduction was confirmed after decomposition (occurring near 170° C.) from the start of temperature increase. From the theoretical moisture value of a reduced glutathione-sodium salt, the crystal obtained in Example 1 was believed to be a monohydrate crystal.

Test Example 3

Hygroscopicity Test

The amorphous solid of a reduced glutathione-sodium salt obtained in (1) of Example 1, and the final crystal of a reduced glutathione-sodium salt obtained in Example 1 were compared for hygroscopicity under the following conditions.

Storage conditions: 40° C., 75% relative humidity (adjusted with saturated brine)

Measurement conditions: About 0.3 g of a sample was weighed with a precision balance, and charged into a plastic container. After being stored under the foregoing storage conditions, the sample was weighed, and the percentage of weight change was calculated.

The results are as follows. The measured sample weight at each time point is relative to the 100% initial weight at the start of testing. In table 5, the symbol "-" means no measurement.

TABLE 5

| Elapsed time (h) | 0 | 0.25 | 2 | 4 | 10 | 20 | 48 |
|---|---|---|---|---|---|---|---|
| Crystal weight (%) | 100 | — | 100.7 | — | 101.9 | 102 | 102.9 |
| Amorphous weight (%) | 100 | 100.7 | 104.1 | 106.2 | 110.2 | 117.3 | 125.8 |

The crystal was less likely to absorb moisture than the amorphous solid, and had more desirable preservation stability.

Example 3

Production of Monohydrate Crystal of Reduced Glutathione-Sodium Salt

A free glutathione crystal (310 g; purchased from KOJIN. Co. Ltd.) was dissolved in water, and the volume was adjusted to 1,000 mL with a sodium hydroxide aqueous solution, which was also used to bring the pH to 6.0. A 250-mL portion of the aqueous solution was used for the next step.

A 100-mL concentrate obtained by concentrating the 250-mL aqueous solution was maintained at 25° C., and 110 mL of 100% methanol was dropped over the course of 1 hour. The crystal obtained in Example 1 (0.75 g) was then added as a seed crystal to form crystals. The crystal slurry was aged at 70° C. for 1 hour, and at 25° C. for 12 hours, and the crystals were filtered off. After draught drying at 25° C., 35.7 g of a reduced glutathione-sodium salt crystal was obtained.

Test Example 4

Powder X-Ray Diffraction Analysis

The reduced glutathione-sodium salt crystal obtained in Example 3 was subjected to powder X-ray diffraction analysis.

The analysis was conducted under the following conditions, and the following measurement conditions were used for the crystal obtained in Example 3.

Analyzer: Horizontal-sample multi-purpose X-ray diffraction device Ultima IV available from Rigaku Measurement Conditions:
X-ray source: CuKα
Measurement wavelength: 1.541 Å
Kα rays were used without being monochromatized with a monochrometer The chart diagram for the crystal obtained in Example 3 was compared with the chart diagram of FIG. 1. The results were very similar, confirming that the crystal obtained in Example 3 had the same crystal form as the crystal obtained in Example 1.

Test Example 5

Single-Crystal X-Ray Structure Analysis

In order to determine the crystal structure, the reduced glutathione-sodium salt crystal obtained in Example 3 was subjected to single-crystal X-ray diffraction (SXRD) using the single-crystal X-ray structure analyzer SuperNova (Agilent Technologies). First, single crystals of a metal salt of reduced glutathione were installed in a diffractometer, and the diffraction image was measured in a room temperature atmosphere or under a stream of an inert gas of a predetermined temperature, using X-rays of a predetermined wavelength. A single-crystal structure was obtained from a combination of the plane index and the diffraction intensity calculated from the diffraction image, after structure determination by direct method, and structure refinement by least squares method [Acta Cryst. A64, 112 (2008)]. The results are summarized in Table 6.

The measurement results confirmed that the crystal was a crystal of a reduced glutathione-sodium salt, and was a monohydrate crystal having a water molecule within the unit lattice. The Flack parameter [Acta Cryst. A39, 876. (1983)] was −0.12 (11), close to zero, confirming that there was no contradiction in the absolute structure revealed by the analysis.

TABLE 6

| Crystal data | |
|---|---|
| Chemical formula | $Na^+ \cdot (C_{10}H_{15}N_3O_8S)^- \cdot H_2O$ |
| $M_r$ | 347.32 |
| Crystal system, space group | Orthorhombic, $P2_12_12_1$ |
| Temperature (K) | 100 |
| a, b, c (Å) | 27.881 (14), 10.818 (5), 4.881 (2) |
| V (Å$^3$) | 1472.2 (12) |
| Z | 4 |
| Emission type | CuKα |
| μ (mm$^{-1}$) | 2.63 |
| Crystal size (mm) | 0.16 × 0.04 × 0.03 |
| Data Collection | |
| Diffractometer | Agilent SuperNova CCD diffractometer |
| Absorption correction | None |
| Number of observed independent [I > 2σ (I)] reflections | 5142, 2834, 1237 |
| $R_{int}$ | 0.1442 |
| $(\sin\theta/\lambda)_{max}$ (Å$^{-1}$) | 0.625 |

TABLE 6-continued

| Refinement | |
|---|---|
| R[F² > 2σ(F²)], wR(F²), S | 0.1106, 0.3262, 1.006 |
| Number of reflections | 2834 |
| Number of parameters | 217 |
| H atom process | H-atom parameters constrained |
| Δρ$_{max}$*, Δρ$_{min}$ (e Å⁻³) | 0.46, −0.47 |
| Absolute structure | Flack x determined using 1119 Friedel pairs (Flack, 1983) |
| Absolute structure parameter | −0.12 (11) |

Example 4

Production of Anhydrous Crystal of Reduced Glutathione-Sodium Salt

The monohydrate crystal of a reduced glutathione-sodium salt (5.0 g) obtained in Example 3 was dried by draught drying at 105° C. for 20 hours to obtain a white crystal (4.6 g).

Test Example 6

Moisture Content Measurement

The crystal obtained in Example 4 was measured under the following conditions.
Measurement device: Automatic moisture measurement device AQV-2200 (Hiranuma Sangyo Co., Ltd.)

The moisture content of the crystal was 1.3 weight % as measured by the Karl Fischer method. A comparison with the theoretical moisture content revealed that the reduced glutathione-sodium salt crystal was an anhydrous crystal of a reduced glutathione-sodium salt.

Test Example 7

Powder X-Ray Diffraction Analysis

The anhydrous crystal of a reduced glutathione-sodium salt obtained in Example 4 was subjected to powder X-ray diffraction analysis using the same procedure used in the Test Example 4 above. The result is presented in Table 7. The chart diagram of the powder X-ray diffraction analysis is shown in FIG. 2.

TABLE 7

| 2θ (°) | Intensity (cps) | Relative intensity |
|---|---|---|
| 15.54 | 5983 | 13 |
| 17.46 | 8167 | 18 |
| 18.32 | 10533 | 23 |
| 19.26 | 10458 | 23 |
| 19.70 | 11833 | 26 |
| 20.28 | 19883 | 44 |
| 20.52 | 17642 | 39 |
| 21.26 | 15867 | 35 |
| 22.48 | 13567 | 30 |
| 25.02 | 16358 | 36 |
| 25.92 | 46167 | 100 |
| 26.66 | 16067 | 35 |
| 27.28 | 20175 | 44 |
| 28.08 | 14058 | 31 |
| 28.74 | 9308 | 21 |
| 29.64 | 8608 | 19 |
| 33.56 | 13100 | 29 |
| 34.38 | 8008 | 18 |
| 35.58 | 6108 | 14 |
| 38.40 | 7167 | 16 |
| 41.18 | 6608 | 15 |
| 43.40 | 5750 | 13 |

As shown in Table 7, the diffraction angles in the result of the powder X-ray diffraction of the crystal obtained in Example 4 were slightly different from the diffraction angles observed for the monohydrate crystal of a reduced glutathione-sodium salt obtained in Example 1. This is probably due to desorption of water molecules taking place without accompanying large changes in the position and conformation of molecules from the monohydrate crystal of a reduced glutathione-sodium salt in the drying process, and the resulting change in the intensity of each diffraction peak occurring with slight contraction of crystal lattice. Similar changes can be seen in reference document (Cryst. Growth Des. Vol. 16, p 1543, 2016).

While the invention has been described in detail and with reference to specific embodiments thereof, it will be apparent to one skilled in the art that various changes and modifications can be made therein without departing from the spirit and scope of the invention. The present application is based on Japanese Patent Application No. 2015-074084 filed on Mar. 31, 2015, and the contents are incorporated herein by reference.

INDUSTRIAL APPLICABILITY

According to the present invention, a metal salt crystal of reduced glutathione useful for, for example, products such as health-aid food, pharmaceuticals, and cosmetics, or as a raw material, an intermediate, or the like of such products is provided.

The invention claimed is:

1. A crystal of a metal salt of reduced glutathione, which is a monohydrate crystal of a salt of reduced glutathione and sodium, and has peaks at a diffraction angle (2θ) of 19.90°±0.20°, 25.58°±0.20°, and 26.88°±0.20° in powder X-ray diffraction.

2. The crystal according to claim 1, which has peaks also at a diffraction angle (2θ) of 20.16°±0.20°, 24.68°±0.20°, 26.30°±0.20°, 27.68°±0.20°, and 33.20±0.20° in powder X-ray diffraction.

3. The crystal according to claim 2, which has peaks also at a diffraction angle (2θ) of 17.90°±0.20°, 20.86°±0.20°, 22.10°±0.20°, and 25.30°±0.20° in powder X-ray diffraction.

4. The crystal according to claim 3, which has peaks also at a diffraction angle (2θ) of 6.42±0.20°, 18.90±0.20°, and 29.30±0.20° in powder X-ray diffraction.

5. A crystal of a metal salt of reduced glutathione, which is a monohydrate crystal of a salt of reduced glutathione and sodium, and has the following brief unit cell parameters: a=27.881 Å, b=10.818 Å, c=4.881 Å, α=90°, β=90°, γ=90°, V=1472.2 Å³, and Z=4 with a space group P2$_1$2$_1$2$_1$ (#19), as measured by single-crystal X-ray structure analysis at −173° C.

6. A method for producing a crystal of a metal salt of reduced glutathione, the method comprising dissolving a free form of reduced glutathione in a metal hydroxide aqueous solution, and adjusting the pH of the solution to 5.0 to 8.0 to obtain an aqueous solution of a metal salt of reduced glutathione; concentrating the resulting aqueous solution, and gradually adding a C1 to C6 alcohol to the concentrated aqueous solution in small portions in an amount 0.1 to 3 times the amount of the concentrated aqueous solution; and adding a crystal of a metal salt of reduced glutathione as a seed crystal to precipitate a crystal of a metal salt of reduced glutathione.

7. The method for producing a crystal of a metal salt of reduced glutathione according to claim 6, wherein the C1 to C6 alcohol is methanol or ethanol.

8. The method for producing a crystal of a metal salt of reduced glutathione according to claim 6, wherein the crystal of a metal salt of reduced glutathione is a monohydrate crystal of a salt of reduced glutathione and a metal selected from the group consisting of sodium, potassium, calcium, and magnesium.

9. The method for producing a crystal of a metal salt of reduced glutathione according to claim 6, wherein the crystal of a metal salt of reduced glutathione is a monohydrate crystal of a reduced glutathione-sodium salt.

* * * * *